United States Patent
Falk et al.

[11] Patent Number: 6,080,124
[45] Date of Patent: Jun. 27, 2000

[54] PATELLA STRAP METHOD

[75] Inventors: Rhonda M. Falk, Tamarac; William L. McNally, Weston, both of Fla.

[73] Assignee: FLA Orthopedics, Inc., Miramar, Fla.

[21] Appl. No.: 09/375,622

[22] Filed: Aug. 17, 1999

Related U.S. Application Data

[62] Division of application No. 09/028,607, Feb. 24, 1998.

[51] Int. Cl.[7] .............................. A61F 13/00; A61F 5/00
[52] U.S. Cl. ................................. 602/26; 602/62; 602/23
[58] Field of Search .................................. 602/5, 20, 23, 602/26, 60, 61, 62, 63, 19; 128/856, 887, 892; 607/96, 108, 112; 2/22, 24, 62

[56] References Cited

U.S. PATENT DOCUMENTS

| | | | |
|---|---|---|---|
| D. 352,114 | 11/1994 | Nicholson | D24/190 |
| 4,116,236 | 9/1978 | Albert . | |
| 4,334,528 | 6/1982 | Gauvry . | |
| 4,466,428 | 8/1984 | McCoy . | |
| 4,777,946 | 10/1988 | Watanabe et al. . | |
| 4,805,620 | 2/1989 | Meistrell . | |
| 5,139,015 | 8/1992 | Morneau | 602/62 |
| 5,232,424 | 8/1993 | Pearson et al. | 482/106 |
| 5,417,646 | 5/1995 | Gauvry | 602/26 |
| 5,466,251 | 11/1995 | Brunson et al. | 607/112 |
| 5,759,167 | 6/1998 | Shields, Jr. et al. | 602/26 |

FOREIGN PATENT DOCUMENTS

| | | | |
|---|---|---|---|
| 3416231 | 11/1985 | Germany | 602/63 |

*Primary Examiner*—Kim M. Lee
*Attorney, Agent, or Firm*—Jack E. Dominik

[57] ABSTRACT

A patella strap which the patella strap has a forward patella press which optionally includes a horse shoe shaped gel. Laterally of the patella press on both sides, buckles are provided which assist in securing the tension of the strap, provision is made for an angulated tension control which permits the patella strap to be used in the inferior or superior position with equal facility. The elasticized patella press allows individual tension control. The elastic patella press also provides the pocket for securing the viscoelastic insert. The band which engages the laterally positioned buckles optionally, but desirably, has an underlying leather like strap which prevents the buckle from contacting the skin of the body. The rear mounting body strap is inserted at both ends into the guide of the buckle, opposing the opening to receive the elasticized patella press which holds the patella engaging portion in place. The rear strap is intentionally non-elastic or in-elastic, and the two end portions have removable securing members which engage the outer surface of the strap after the end tabs have been reversibly folded to the buckle.

4 Claims, 2 Drawing Sheets

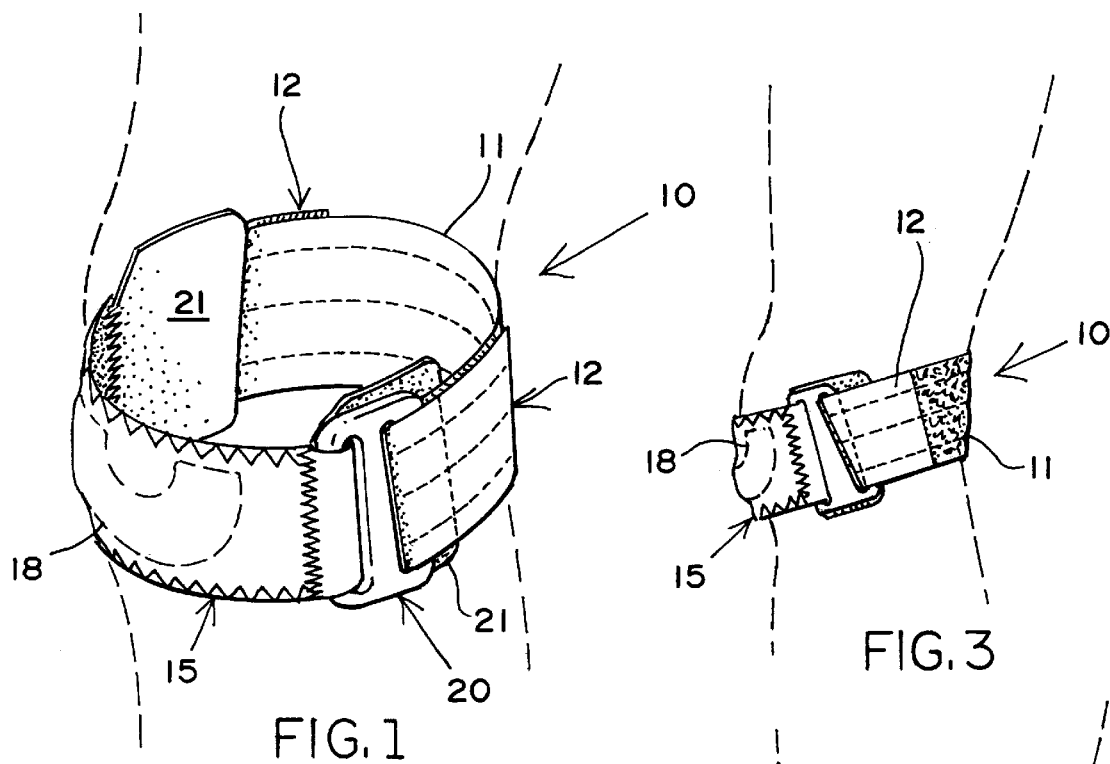
FIG. 1
FIG. 3
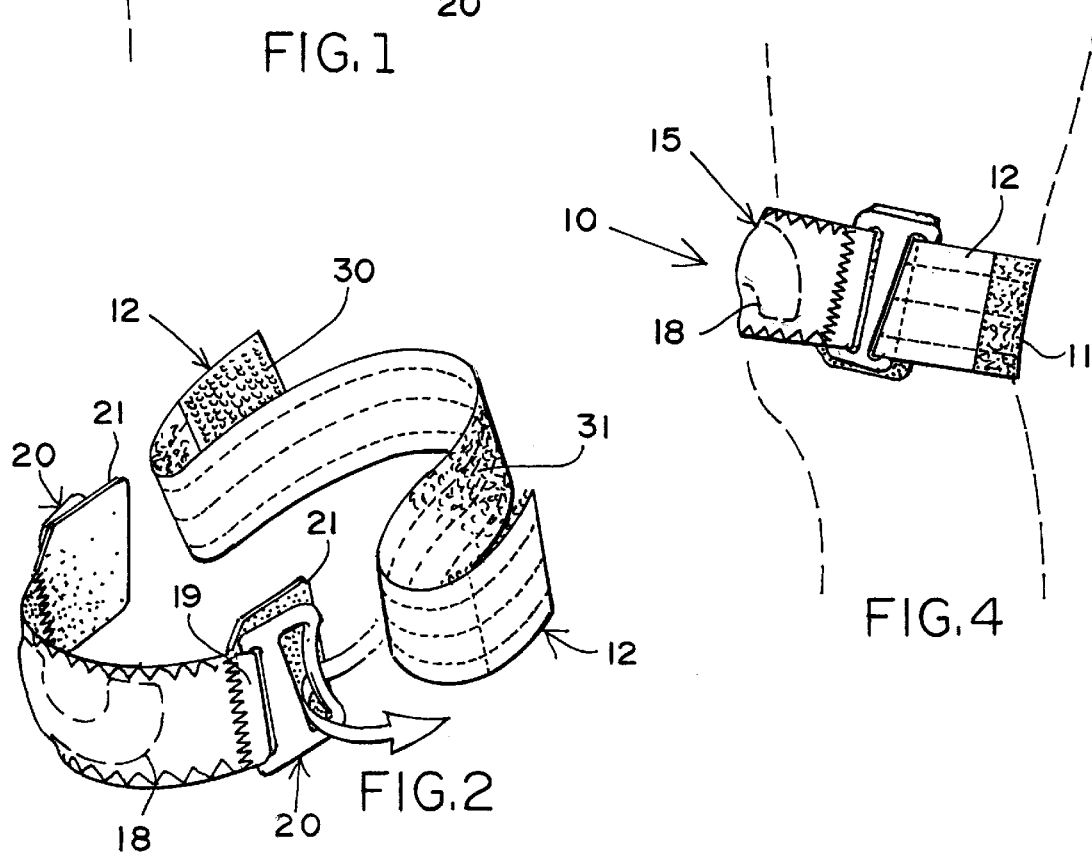
FIG. 2
FIG. 4

PATELLA STRAP METHOD

RELATED APPLICATION

This application is a divisional of application Ser. No. 09/028,607, filed Feb. 24, 1998.

FIELD OF THE INVENTION

The present invention relates to patella straps commonly used where the patella or knee cap of an individual requires pressure to raise or lower the patella.

BACKGROUND OF THE INVENTION

In most instances when a patella strap such as that identified in U.S. Pat. No. 4,334,528 is employed, the support is applied to the lower portion of the patella. The strap of U.S. Pat. No. 5,417,646, on the other hand, supports above and below the patella. This is known as an inferior application. The patella strap applies pressure on the patellar tendon below the knee cap or patella, which helps guide the patella in a femoral groove for improved tracking. Improved tracking, in turn, relieves pressure and discomfort and helps to prevent eventual degeneration. More specifically, the conditions for which a patella strap is typically used include Chondromalacia Patella Syndrome (Runners Knee), Patellar Tendonitis (Jumpers Knee), Osgood-Schlatter's Disease and Iliotibial Band Syndrome.

Alternatively, a patella strap in the superior usage applies pressure on the quadriceps muscles above the knee cap. This helps to insure that the patella glides easily against the thigh bone for improved patella tracking. Improved tracking helps relieve pressure and discomfort and helps prevent eventual degeneration. A condition for which a superior usage of a patella strap is indicated typically involves weakened quadriceps muscles.

Patella straps such as exemplified in U.S. Pat. No. 4,334,528 do not distribute the pressure over a large pressure area, nor is provision for cushioning provided. In addition, the subject prior art patella strap is primarily dedicated to inferior usage, and not superior usage. Furthermore, pressure adjustment is awkward because no mechanical advantage is provided for tensioning the band.

SUMMARY OF THE INVENTION

The present invention is directed to a patella strap and method in which the patella strap has a forward patella press which optionally includes a horse shoe shaped gel. Laterally of the patella press on both sides, buckles are provided which assist in securing the tension of the strap, provision is made for an angulated tension control which permits the patella strap to be used in the inferior or superior position with equal facility. Desirably a viscoelastic horse shoe shaped insert allows conforming compression to individual patella shapes at the point of application. The elasticized patella press allows individual tension control. The elastic patella press also provides the pocket for securing the viscoelastic insert. The band which engages the laterally positioned buckles optionally, but desirably, has an underlying leather like strap which prevents the buckle from contacting the skin of the body. The rear mounting body strap is inserted at both ends into the guide of the buckle, opposing the opening to receive the elasticized patella press which holds the patella engaging portion in place. The rear strap is intentionally non-elastic or in-elastic, and the two end portions have removable securing members which engage the outer surface of the strap after the end tabs have been reversibly folded to the buckle. The method of the invention is directed to selecting the type of patella pressure desired, whether inferior or superior. Thereafter, a patella strap having the general characteristic of one with an elastic patella press holding a gel like member, and an inelastic band to the rear passing through an angulated buckle. Optionally when the buckle guide is angled, the strap is reversible from that inferior to superior position. The wearer firstly applies the elastic press portion in a position inferior or superior to the patella or knee cap. Then, at that point, or previously, the mounting strap which is relatively in-elastic is positioned and inserted to the angulated portion of the buckle. Thereafter, one side or both sides of the body strap are pulled until the desired tension is in the strap assembly and the desired pressure is inferior or superior to the patella. The final step in the method resides in the closing of the relatively in-elastic strap behind the knee in a central position where the width of the strap applies pressure across a large area of the rear portion of the knee to thereby reduce any tendency for constricting blood flow, adverse pressure on the nerves, and otherwise just disrupting the normal function of the knee by being supported.

In view of the foregoing it is a principal object of the present invention to provide a patella strap which is universal in size, and can be applicable to knees with a circumference of 10 inches through 19 inches.

A related but important object of the present invention is to provide for reversibility of the patella strap so that it can be applied for inferior or superior applications.

A further object of the present invention is related to its reversibility, and derives from the utilization of an angulated tension control strap and buckle which provides for a 5 degree to a 10 degree offset angle. This permits the in-elastic band to be urged upwardly on the thigh or downwardly on the calf, depending upon the application.

Yet a further object of the present invention is to provide a visco-elastic U-shaped or horse-shaped insert which allows conformation by way of compression to individual knee structures at the point of application.

Yet another object of the present invention resides in fulfilling the foregoing objectives with a patella strap which is inherently inexpensive to manufacture and cost justified, in view of its numerous advantages, and is reversible in application.

DESCRIPTION OF A ILLUSTRATIVE EMBODIMENT

Further object and advantages of the present invention will become apparent as the following description of an illustrative embodiment takes place, and in which:

FIG. 1 is a front perspective of a typical knee, in phantom lines, illustrating the illustrative patella strap in the inferior position;

FIG. 2 is a view substantially identical to that of FIG. 1 but disclosing the patella strap in an exploded perspective view;

FIG. 3 is a lateral view from the side of the knee of the patella strap in the inferior position. It shows in dotted lines the angulated buckle and the knee;

FIG. 4 is a view similar to FIG. 3, but showing the patella strap in the superior position and also illustrating in dotted lines the angulated position of the buckle and the knee;

DESCRIPTION OF A PREFERRED EMBODIMENT

The subject patella strap 10 is shown in FIGS. 1 and 2. FIG. 3 shows the inferior application FIG. 4 shows the superior application. The side view of the patella strap, shown in FIG. 2, is the same as in the inferior position, with the body strap 11, by means of its end tabs 12, penetrating the buckle and reversely folded to secure the same in place.

Figure 5:
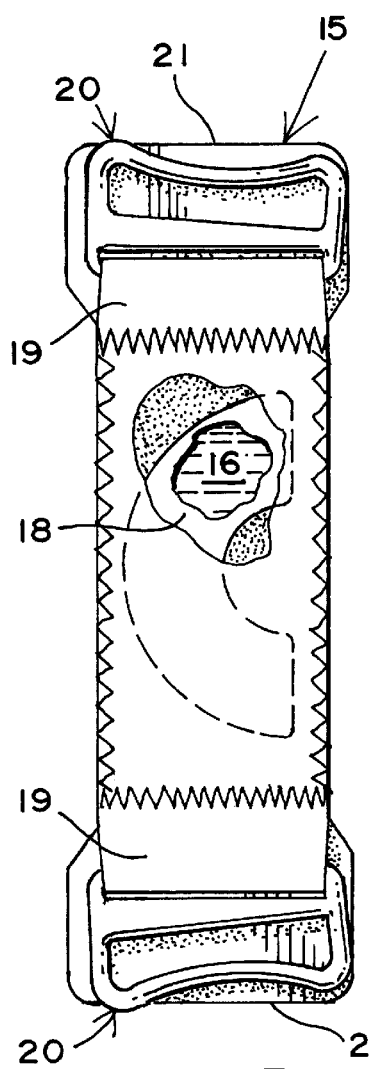
FIG. 5 is a plan view one side of the entire patella strap central elastic portion.
Figure 6:
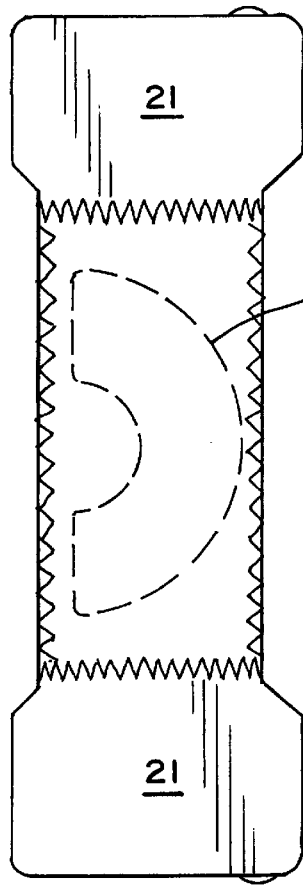
FIG. 6 is a plan view of the elastic portion taken from the rear of FIG. 5 showing the offset flaps which underline the buckle.
Figure 7:
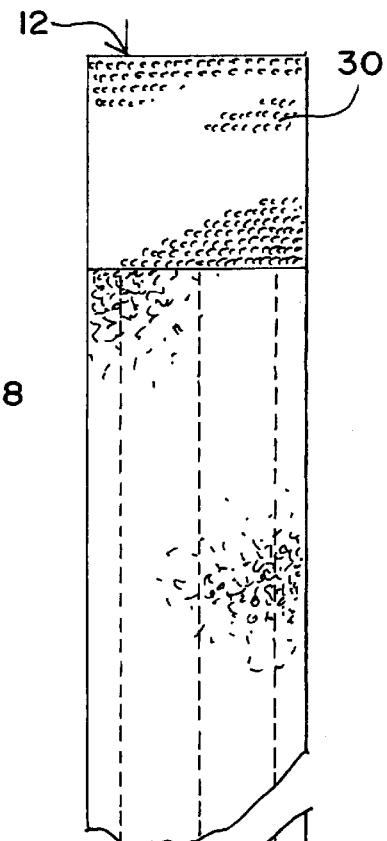
FIG. 7 is a plan view of one of the body straps.

Turning now to FIG. 5, it will be seen that the elastic patella press 15 is preformed of an elastic fabric which is stitched around all 4 sides. Interiorly the horse shoe shaped gel 16 is held in a gel pocket 18 provided by the patella press 15. End loops 19 in the elastic patella press 15 are provided to secure the same to the buckle 20. To be noted FIG. 8 is that the buckles each have an end loop slot 22 for mounting the same to the end loops 19 of the patella press 15.

Figure 8:
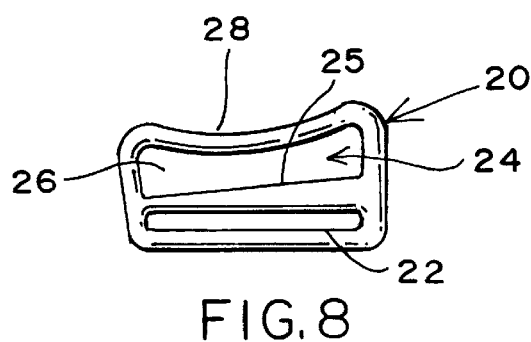
FIG. 8 is a plan view of the buckle.

In accordance with one aspect of the invention, as shown in FIG. 8, a desirably angled guide 24 with an angled guide base 25 is provided to define a guide enclosure 26 in the buckle 20. The guide 24 being angled at an angle 5 to 10 degrees, insures that the body strap 11 presses upwardly or downwardly depending upon whether the inferior or superior position is preselected. The buckle shield 21, provided beneath the buckle 20, covers the area beneath the buckle 20 and thereby inhibits the pressure of the relatively hard plastic buckle 20 from pressing against the knee, but rather distributes the pressure over the area of the buckle shield 21. The closure cap 28 of the buckle 20 is curved on its outside to assist in the tensioning when applied.

The method of the invention, as shown in FIGS. 1–4, includes the steps of applying the subject patella strap 10 which involves positioning the elastic patella press 15 firstly in the inferior or superior position. The user adjusts the patella press 15 until the horse-shoe-shaped viscoelastic gel 16 is oriented above or below the patella, as desired. Previously or thereafter the body strap 11, which is generally in-elastic, is secured to the two buckles 20 at either end of the same, and through the guide base 25. Then with both hands, or one hand at a time, the end tabs 12 are secured to the rear face of the body strap 11. The end tabs 12 have on their underneath side, a loop 31 or hook 30 mating engagement material to match the mating engagement material on the body strap 11 which faces the end tabs 12 when they are reversed. The tension provided by the user is initially adjusted for comfort, and at a level which is intended not to inhibit circulation. During use, of course, the tension can be increased or decreased easily by adjusting one or the other or both of the end tabs 12.

While materials are not necessarily critical to the subject invention, in a desirable commercial embodiment the body strap 11 is formed of the following material:

Velcro® double faced loop (2")

The end tabs 12 are an extension of the body portion of the strap, but secured there beneath is a mating engagement material having the following additional characteristics:

2"×2" Velcro® hook material.

The body strap 11 is formed of a material having the following characteristics:

2" hook compatible material, also soft and plush.

The buckles 20 are molded of polypropylene having a dimensional limitation primarily dictated by the height of the patella press. The underling buckle shields 21 are formed of:

Leather.

The patella press 15 and its interior packet is formed of:

Velcro® velstretch 2".

Desirably the horse-shoe-shaped gel visco-elastic member 16 is formed of the following material and by the following method:

Molded visco-elastic material with felt background.

As it will be noted in the drawings stitching appears on the lateral edges of the gel pocket, the ends of the gel pocket where the loop 19 is provided to receive the buckle 20, and such stitching is characterized as follows:

Zig Zag stitch.

In a commercial embodiment the dimensions of the various elements have the following ranges for the elastic press 15:

length=5½", width=2", thickness=0.5".

The in-elastic strap, desirably, has the following dimensions:

17" (L)×2" (W).

Finally, the buckles have a dimension control by the press pocket or the strap, or reversely, the press pocket controls the length and essentially the width of the buckle.

It will be understood that various changes in the details, materials and arrangements of parts which have been herein described and illustrated in order to explain the nature of the invention, may be made by those skilled in the art within the principle and scope of the invention as expressed in the appended claims.

What is claimed is:

1. A method of applying a reversible patella strap, comprising the steps of:

providing a patella strap comprising in combination, an elongate body strap having end tabs at each end of the body strap, said end tabs having a releasable securing fit when the end tabs are reversibly folded over the body; a patella press which is essentially elastic and contains a pocket and a cushion member therein, and buckles for receiving the body strap in interlocking relationship to thereby secure the patella strap to the knee, said buckles each having an angulated slot;

positioning the patella press in an inferior position on the knee adjusted to engage the patella or patella tendon;

securing the body strap to the buckles on a lateral portion of the press and reversely folding the end tabs thereover;

tensioning the body strap to the desired tension, and thereafter securing the strap in place by positioning the end tabs on a rear portion of the body strap.

2. A method of applying a reversible patella strap, comprising the steps of:

providing a patella strap comprising in combination, an elongate body strap having end tabs at each end of the body strap, said end tabs having a releasable securing fit when the end tabs are reversibly folded over the body; a patella press which is essentially elastic and contains a pocket and a cushion member therein, and means for receiving the patella press strap in interlocking relationship to thereby secure the patella strap to the knee, said means for receiving each having an angulated slot;

positioning the patella press in a superior position on the knee adjusted to engage the patella or quadriceps muscles;

securing the body strap to the means for receiving on a lateral portion of the press and reversely folding them thereover;

tensioning the body strap to the desired tension, and thereafter securing the strap in place by positioning the end tabs on a rear portion of the body strap.

3. A method of applying a reversible patella strap, comprising the steps of:

provide a patella strap comprising in combination, an elongate body strap having end tabs at each end of the body strap, said end tabs having a releasable securing fit when the end tabs are reversibly folded over the body; a patella press which is essentially elastic and contains a pocket and a cushion member therein, and means for receiving the patella press strap in interlocking relationship to thereby secure the patella strap to the knee, said means for receiving having an angulated slot;

positioning the patella press in an inferior or superior position on the knee adjusted to engage the patella or quadriceps muscles;

securing the body strap to the means for receiving on a lateral portion of the press and reversely folding them thereover;

tensioning the body strap to the desired tension, and thereafter securing the strap in place by positioning the end tabs on a rear portion of the body strap.

4. A method of applying a reversible patella strap, comprising the steps of:

providing a patella strap comprising in combination, an elongate body strap having end tabs at each end of the body strap, said end tabs having a releasable securing fit when the end tabs are reversibly folded over the body; a patella press which is essentially elastic and contains a pocket and a cushion member therein, and means for receiving the patella press strap in interlocking relationship to thereby secure the patella strap to the knee, said means for receiving having an angulated slot;

positioning the patella press in an superior position on the knee adjusted to engage the patella or quadriceps muscles;

securing the body strap to the means for receiving on lateral portion of the press;

tensioning the body strap to the desired tension, and thereafter securing the strap in place by positioning the end tabs on a rear portion of the body strap.

* * * * *